United States Patent [19]
Clester et al.

[11] Patent Number: 5,743,730
[45] Date of Patent: Apr. 28, 1998

[54] DENTAL PORCELAIN SHADING GUIDE AND METHOD OF USE THEREFORE

[76] Inventors: Kenneth E. Clester; Karen L. Clester, both of 3803 McCain Loop, Anchorage, Ak. 99503

[21] Appl. No.: 647,448

[22] Filed: May 7, 1996

[51] Int. Cl.$^6$ ................................................. A61C 19/10
[52] U.S. Cl. .......................... 433/26; 434/263; 434/269
[58] Field of Search .............................. 433/26; 434/85, 434/88, 263, 269, 368, 416

[56] References Cited

U.S. PATENT DOCUMENTS

| | | | |
|---|---|---|---|
| 396,381 | 1/1889 | Yaggy | 434/269 |
| 1,582,122 | 4/1926 | Clapp | 433/26 |
| 3,492,743 | 2/1970 | Schmidt | 434/88 |
| 3,889,397 | 6/1975 | Flood | 434/88 |
| 4,608,015 | 8/1986 | Smigel | 433/26 |
| 5,004,417 | 4/1991 | Giarmita | 433/26 |
| 5,240,414 | 8/1993 | Thompson | 433/26 |
| 5,494,442 | 2/1996 | Hecht | 434/269 |

FOREIGN PATENT DOCUMENTS

| | | | |
|---|---|---|---|
| 1376650 | 9/1964 | France | 434/269 |

*Primary Examiner*—Ralph Lewis
*Attorney, Agent, or Firm*—Michael J. Tavella

[57] ABSTRACT

A color rendering system for obtaining accurate tooth color. The device has a base sheet, with various tooth outlines printed thereon. Above the base sheet are a number of clear sheets made of mylar, or similar type material. These sheets are then collected and formed into a pad. Three sheets can be used, thereby giving four layers of color, which is sufficient for most cases. Additional clear sheets can be added, however. The dentist can then mark each with the placement of color for a particular layer. When finished, the sheets overlap, providing a detailed picture of tooth color using the four factors discussed above, and the positions of those colors within the tooth.

2 Claims, 8 Drawing Sheets

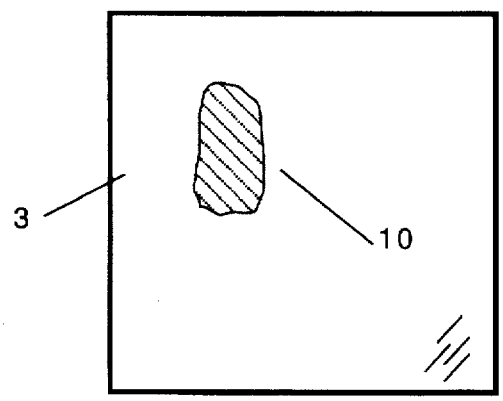
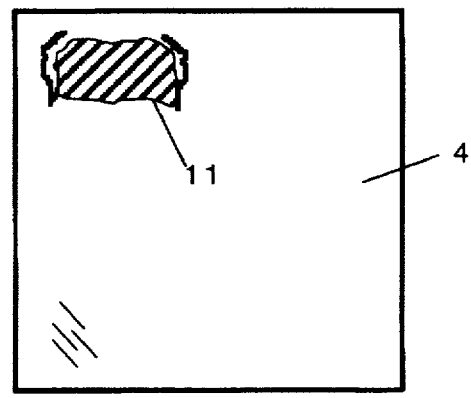
Figure 8  Figure 9
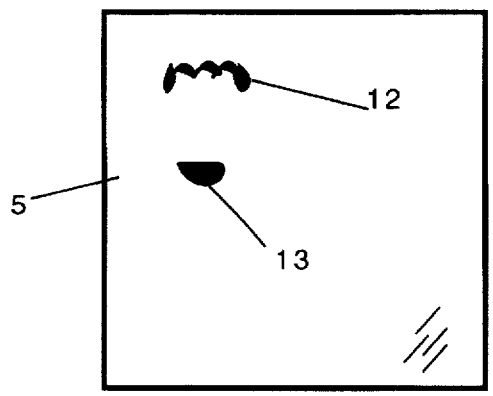
Figure 10

DENTAL PORCELAIN SHADING GUIDE AND METHOD OF USE THEREFORE

This invention relates to dental porcelain shading guides and particularly to dental porcelain shading guides using overlays to develop color depth and levels of shading.

BACKGROUND OF THE INVENTION

Ever since dentists and dental technicians have been able to create dental prostheses such as bridges, crowns and he like, the art has been faced with the problems of matching the color of the prosthesis to the patient's other teeth. Tooth color is an expansive subject. There are many different shades of color found in a tooth. Also, there are other characteristics of color often examined in the art. Four key aspects of color are often used: hue, value, chroma, and translucency. Each of these aspects of color must be carefully measured for a given tooth before a good color match can be made.

Unfortunately, color matching is not an easy task. Moreover, dentists must usually make the color determinations quickly using his or her best visual impressions of the tooth. To help in this color matching and to provide a record for the dental lab technician, who must color the prosthesis from the dentist's description, many devices have been developed. An early device is U.S. Pat. No. 1,582,122 to Clapp, which uses color wheels to compare skin tones to the patient's skin. Once a suitable match is found, the user consults a chart to find the appropriate tooth color. A number of patents use color strips of various types for comparisons. These devices are used by holding a strip near the tooth until a suitable match is found. Examples of these strips are found in U.S. Pat. No. 4,541,801, 4,810,193, 4,802,850, and 4,978, 296.

U.S. Pat. No. 4,608,015 teaches use of overlapping color wheels to help determine tooth color. A lower disk corresponds to the different tooth coloring. A transparent disk is placed over the lower disk and is rotated until a suitable color match is found.

U.S. Pat. No. 5,240,414 attempts to develop a color match that has depth, an important element in color matching. This device has 42 pieces that can be assembled into a model tooth. The number of pieces corresponds to different colors and can be placed on the model where the colors appear on the real tooth. Unfortunately, the number of pieces and the complexity of the device make it impractical for actual use in the dentist office or the lab.

Finally, U.S. Pat. No. 5,004,417 teaches using sheets of paper that have tooth outlines drawn on them to mark tooth color using a set of colored pencils. Using the outlines, the dentist can quickly shade in color on different areas on the sheet to correspond to the desired color. The problem here is that there is no easy way to show layers of color on this flat sheet.

SUMMARY OF THE INVENTION

While all the devices described above can be used with some success in identifying tooth color, they all lack an important aspect of tooth color. Moreover, in many cases, the process is too labor intensive.

As mentioned above, the color of a tooth is based on four factors. But, more importantly, the tooth color is also dependent on the depth of that color on the tooth. All the prior art discussed above treats a tooth as being a flat surface with no depth or layers of color. Although color matching can be done using this assumption, it is one dimensional at best.

In fact, a tooth is a three dimensional object. The enamel portion of a tooth is approximately 1.5 mm deep. It has up to five layers, each being approximately 0.3 mm deep. These layers are semi transparent. Moreover, color is built up on each layer. So, a person looking at an ordinary tooth is not looking a single flat surface. The color in the tooth is actually layered over three to five layers. Thus, color rendering in a tooth is built up over many layers. Although tooth coloring occurs naturally, it is not unlike the fine art technique of using base colors to "build" the color in a painting, layer by layer, until the surface color is applied.

As a result, it is never enough to merely look at the overall sense of color perceived on a tooth. To achieve the best color match, it is important to record the color of teeth in layers. Once this is done, the porcelain tooth can be colored in layers as well, achieving a high degree of matching and depth.

Using the tools available today, it is impossible to develop the depth of color found in a tooth. The present invention overcomes these difficulties by providing a system whereby tooth color can be built in layers in the field. These notes can then be used in the lab to recreate a near perfect match. The device has a base sheet, with various tooth outlines printed thereon. Above the base sheet are a number of clear mylar, or similar type material, sheets. These sheets are then collected and formed into a pad. Three layers of mylar can be used, thereby giving four layers of color, which is sufficient for most cases. Additional clear sheets can be added, however. The dentist can then mark each with the placement of color for a particular layer. When finished, the sheets overlap, providing a detailed picture of tooth color using the four factors discussed above, and the positions of those colors within the tooth.

It is an object of this invention to produce a system for marking coloration of teeth that enables the user to apply color in layers to properly produce color depth in a tooth.

It is another object of this invention to produce a system for marking coloration of teeth that is easy and quick to use.

It is yet a further object of this invention to produce a system for marking the coloration of teeth that is compact and self contained.

It is yet another object of this invention to produce a system for marking coloration of teeth that enables the user to apply color in layers to properly produce color depth in a tooth without having to use coloring instruments that match the precise colors shown.

BRIEF DESCRIPTION OF THE DRAWINGS

FIG. 8 is a front view of the first marked overlay.

FIG. 9 is a front view of the second marked overlay.

FIG. 10 is a front view of the third marked overlay.

DETAILED DESCRIPTION OF THE INVENTION

Figure 1:
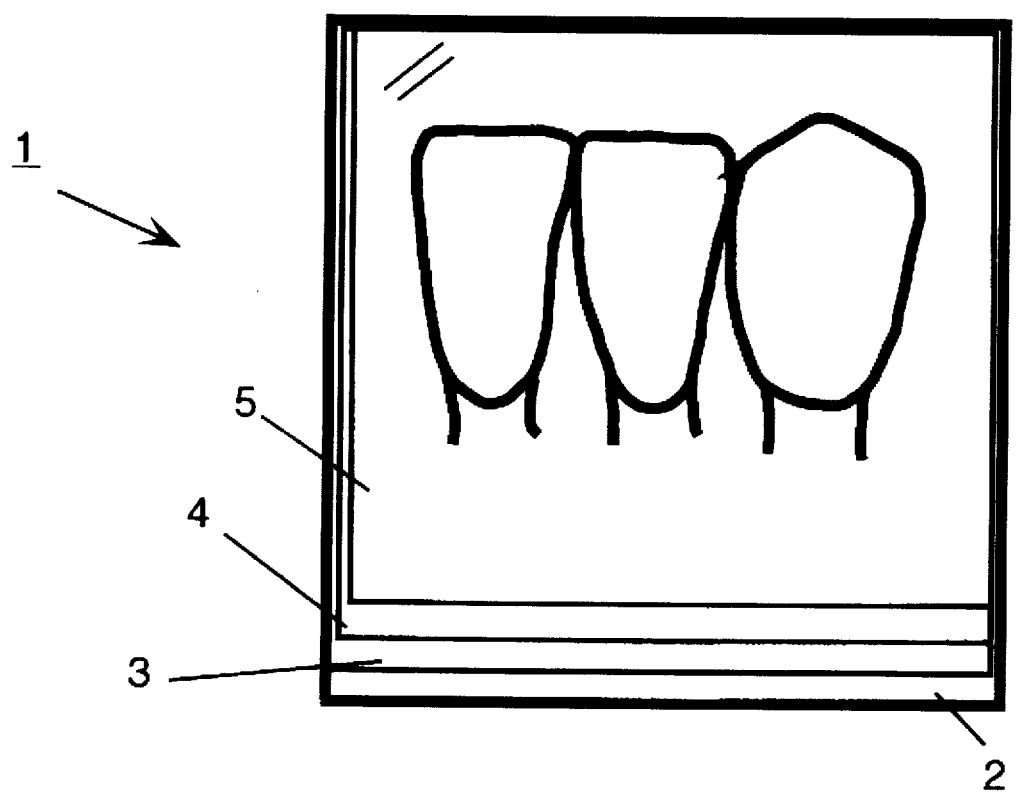
FIG. 1 is a front detail view of the invention as fully assembled.
Figure 2:
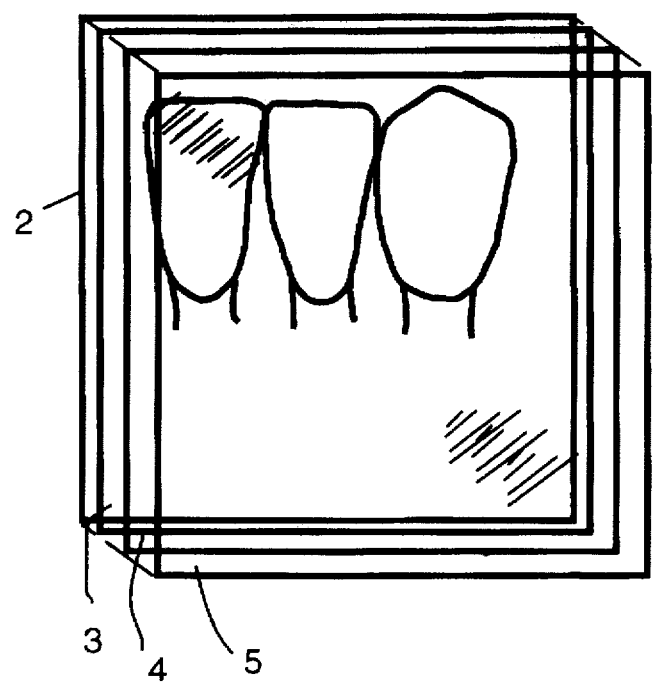
FIG. 2 is an exploded view of the stacked overlays on the base sheet.
Figure 3:
FIG. 3 is a front view of a typical overlay sheet.

Referring now to FIGS. 1, 2, 3, and 4, the invention 1 is shown. It has a base sheet 2, a first overlay sheet 3, a second overlay sheet 4 and a third overlay sheet 5. FIG. 1 shows the invention 1 as fully assembled. FIG. 2 shows an exploded view of the invention 1 showing the layers 2, 3, 4, and 5 stacked up in order. FIG. 3 shows one of the overlay sheets 3, 4, or 5. The overlay sheets 3, 4, or 5 are a rectangle (or square) of clear acetate, mylar or similar material. All the overlay sheets 3, 4, or 5 are identical to that shown in FIG. 3. The overlay sheets 3, 4, and 5 are attached to the base sheet 2 by ordinary means known in the art, such as adhesives, staples or tapes. The overlay sheets 3, 4, and 5 are attached only at the top of the base sheet 2. This allows the overlay sheets 3, 4, and 5 to be lifted at the bottom so that the overlay sheets 3, and 4, that are placed lower in the stack can be used. Overlay sheets 3,4, or 5 can be lifted as needed for marking different layers of color. Of course, the overlay sheets 3, 4, and 5 can be fastened to the bottom or one of the sides of the base 2, if desired. However, these fastening placements are not preferred.

Figure 4:
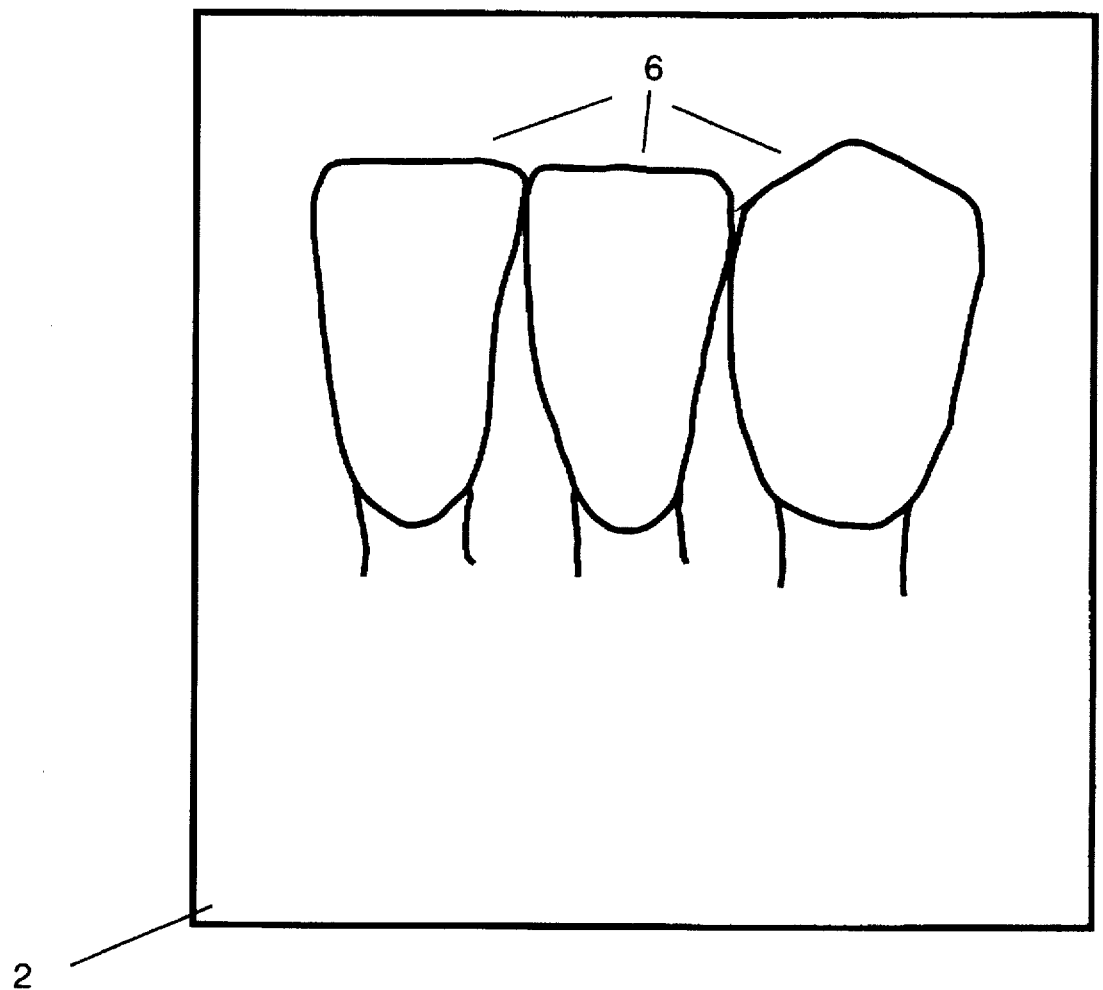
FIG. 4 is a front view of the base sheet of the invention.

FIG. 4 shows the base sheet 2, which is made of paper or heavy card stock and is opaque. Using card stock is preferred because the card stock provides a firm base for marking, especially if the device 1 is held in the hand during the marking process. A number of tooth patterns 6 are printed on the base sheet 2 as shown. In this embodiment, three tooth patterns 6 are shown. However, the number of tooth patterns shown is not critical, as long as the tooth patterns 6 are large enough to produce clear details of the colors involved.

Figure 5:
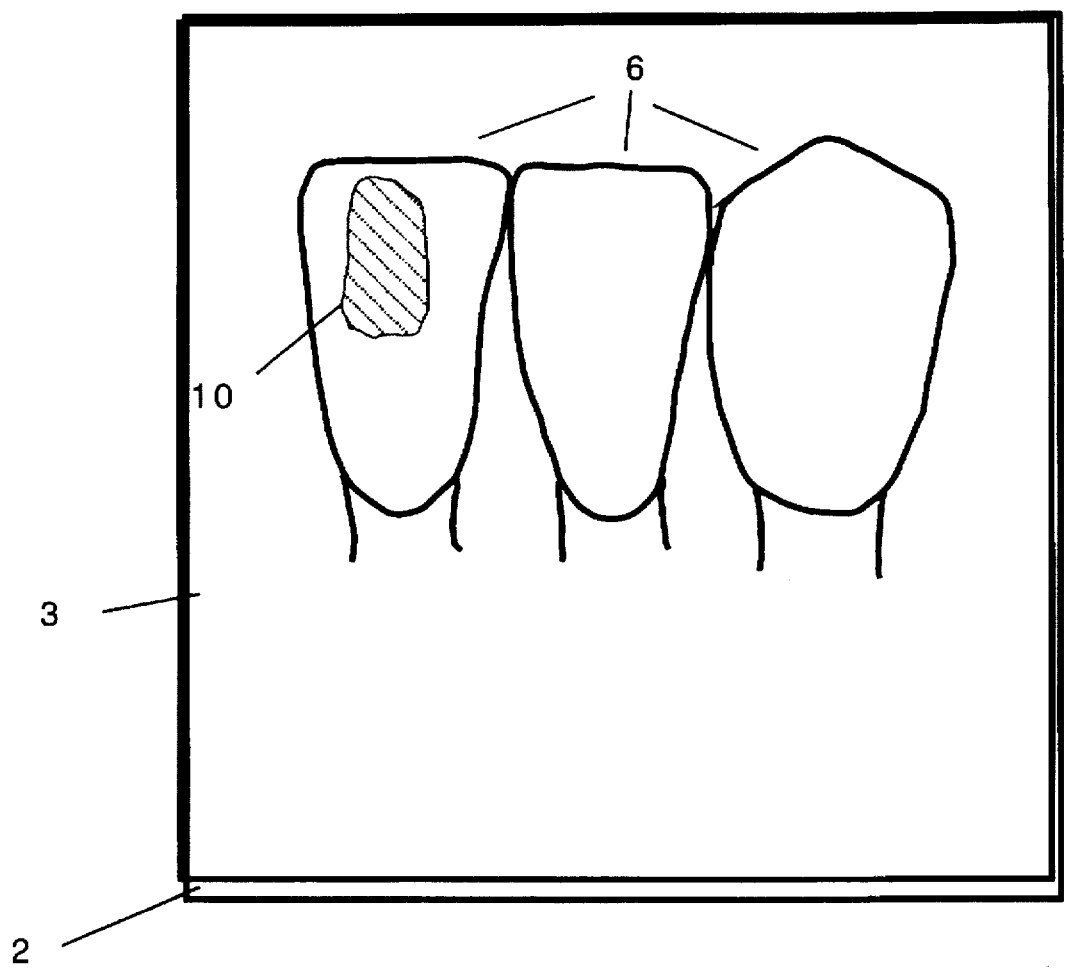
FIG. 5 is a front view of the base sheet with the first marked overlay in place.
Figure 6:
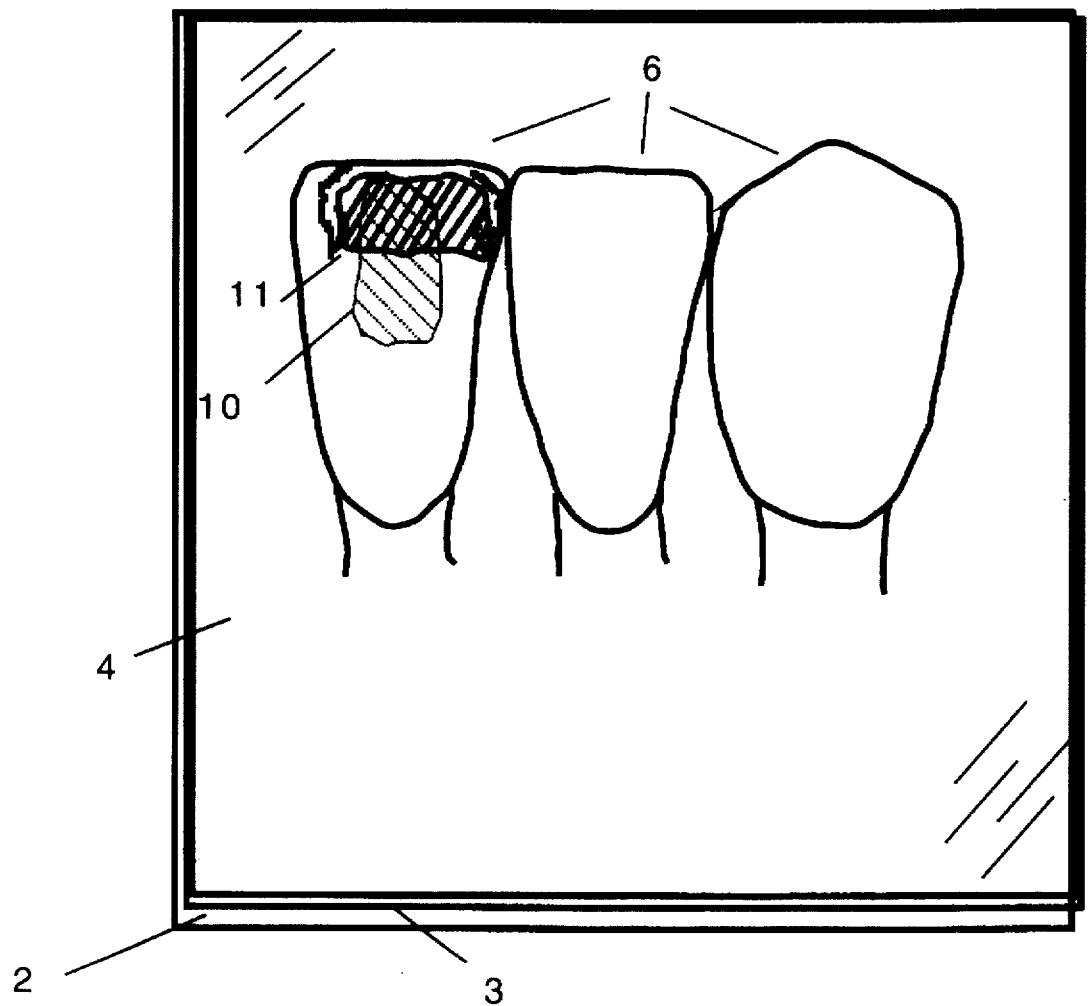
FIG. 6 is a front view of the base sheet with the first and second marked overlays in place.
Figure 7:
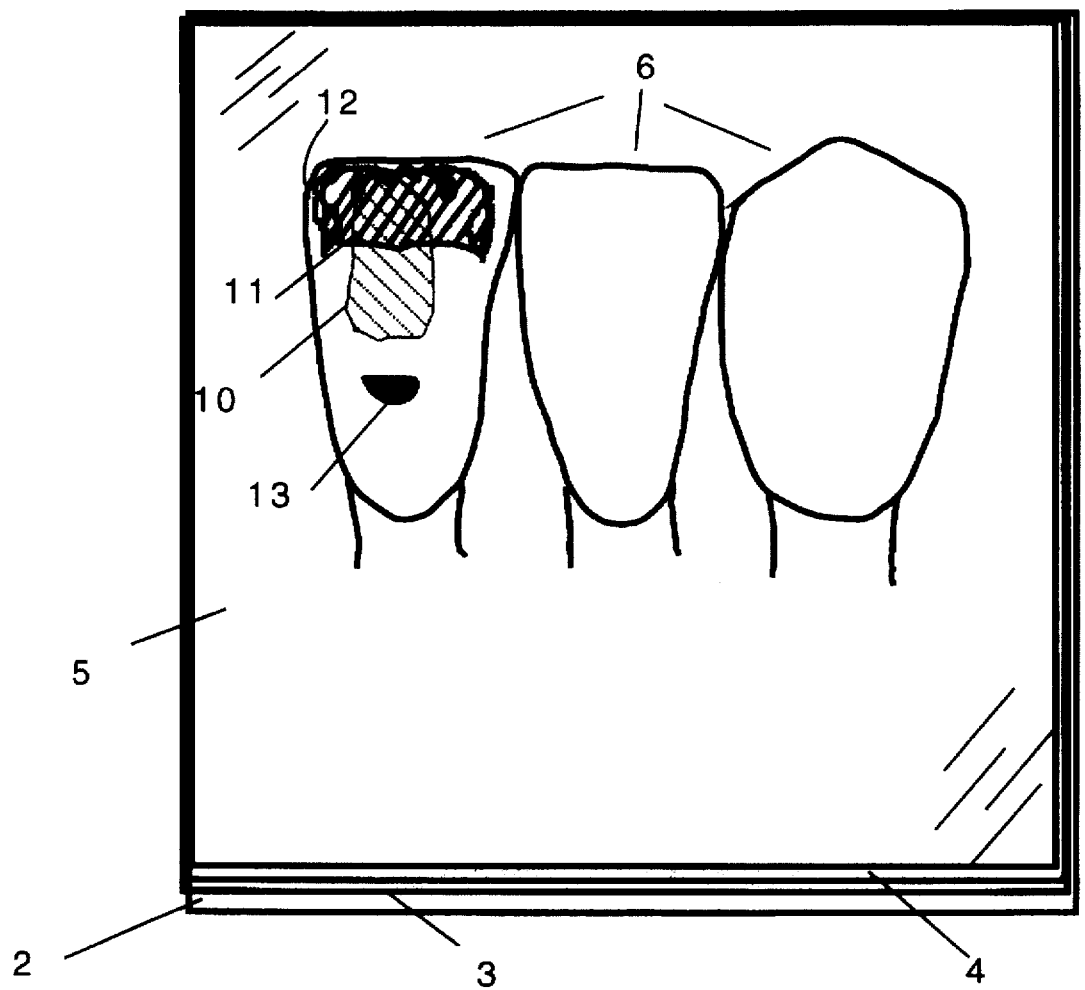
FIG. 7 is a front view of the base sheet with the first, second and third marked overlays in place.

The invention is used by flipping the transparent sheets 3,4, and 5 up so that only the bottom overlay 3 covers the base layer 2 as shown in FIG. 5. With overlay 3 in place, the deepest color pattern 10 is drawn on the overlay as shown in FIG. 5. The precise color description of this mark can be written on the side of the overlay sheet 3, out of the way of the tooth pattern 6. Next, overlay 4 is then placed over both the base layer 2 and overlay sheet 3 as shown in FIG. 6. The next color layer 11 is then sketched in on overlay 4 as shown in FIG. 6. Finally, overlay 5 is placed over the base 2 and other overlay sheets 3, and 4, as shown in FIG. 7. The top-most colorations 12 and 13 can be added to sheet 5 as shown in FIG. 7. FIGS. 8,9 and 10, show the individual overlay sheets 3,4, and 5 with the color markings, 10,11, 12 and 13 shown for clarity.

Figure 11A:
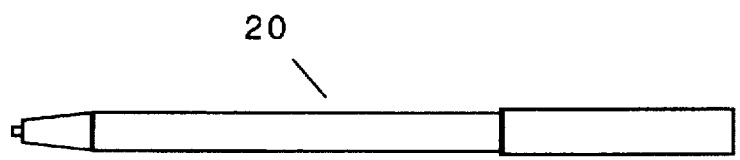
FIG. 11a is a detail view of a pen.
Figure 11B:
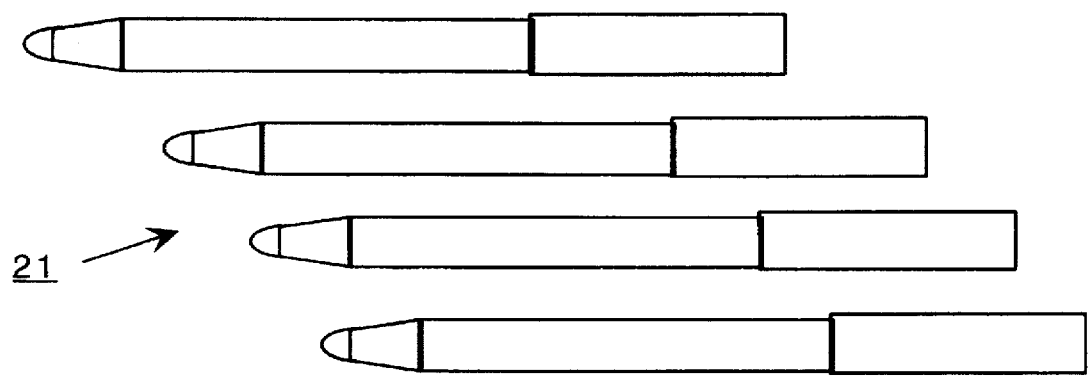
FIG. 11b is a detail view of a set of marking pens.

The color markings are made with a means for marking the sheets, such a pen 20, which is shown in FIG. 11a, or a set or markers 21, which is shown in FIG. 11b.

If desired, color can also be added to the base sheet 2, thereby adding an additional layer of color. In practice, however, three overlay sheets are sufficient for most cases.

This system is simple and fast. This meets the needs of dentists and other technicians, who do not have much time to make color determinations. Moreover, unlike the prior art, which has no easy way of showing depth of color, the instant invention allows rendition of color depth by layering the colors. The instant invention can indicate coloration and depth of color in a fast, efficient manner. Once the colors have been marked on the device 1, the device 1 can be sent to a lab for processing. Here, the lab technician can use the information as to color and depth to make a color match much faster and more accurately than using other devices.

The present disclosure should not be construed in any limited sense other than that limited by the scope of the claims having regard to the teachings herein and the prior art being apparent with the preferred form of the invention disclosed herein and which reveals details of structure of a preferred form necessary for a better understanding of the invention and may be subject to change by skilled persons within the scope of the invention without departing from the concept thereof.

I claim:

1. A method of marking indicating colors of a tooth having a depth, and the depth of placement of the colors, said method using a kit including a device having a base sheet having a top and having at least one outline of a tooth printed thereon, a plurality of overlay sheets, each overlay sheet having a top and a bottom, the top of each overlay sheet being fixedly attached to the top of said base sheet, such that the bottom of each of said plurality of overlay sheets can be lifted, and a means for marking said base sheet and said transparent overlay sheets with color indications, comprising the steps of:

a) determining a deepest color and pattern on a tooth;

b) marking the deepest color and pattern on the overlay sheet closest to said opaque sheet;

c) determining a color and pattern at the next higher level on the tooth; and d) marking the color and pattern on the next higher transparent overlay sheet.

2. The method of marking the color and depth of placement of color for a tooth on a marking device of claim 1 further comprising the step of repeating steps c and d for as many transparent overlay sheets as desired.

* * * * *